United States Patent [19]

Strecker

[11] Patent Number: 4,922,905
[45] Date of Patent: May 8, 1990

[54] DILATATION CATHETER

[76] Inventor: Ernst P. Strecker, Vierordtstrasse 7a, 7500 Karlsruhe 41, Fed. Rep. of Germany

[21] Appl. No.: 194,995
[22] PCT Filed: May 28, 1987
[86] PCT No.: PCT/DE87/00246
  § 371 Date: Mar. 2, 1988
  § 102(e) Date: Mar. 2, 1988
[51] Int. Cl.$^5$ ............................................. A61M 29/02
[52] U.S. Cl. ....................................... 606/195; 623/12
[58] Field of Search .................. 604/96; 128/325, 341, 128/343, 344, 348.1; 623/1, 12

[56] References Cited

U.S. PATENT DOCUMENTS

| | | | |
|---|---|---|---|
| 3,868,956 | 3/1975 | Alfidi et al. | 128/345 |
| 4,434,797 | 3/1984 | Silander | 128/343 |
| 4,448,195 | 5/1984 | LeVeen et al. | 128/344 |
| 4,503,569 | 3/1985 | Dotter | 3/14 |
| 4,512,338 | 4/1985 | Balko et al. | 128/1 |
| 4,580,568 | 4/1986 | Gianturco | 128/345 |
| 4,655,771 | 4/1987 | Wallsten | 623/1 |
| 4,681,110 | 7/1987 | Wiktor | 128/325 X |
| 4,762,128 | 8/1988 | Rosenbluth | 128/343 |
| 4,762,507 | 9/1988 | Fischell et al. | 128/341 X |
| 4,776,337 | 10/1988 | Palmaz | 128/343 |
| 4,800,882 | 1/1989 | Gianturco | 128/343 |

FOREIGN PATENT DOCUMENTS

| | | |
|---|---|---|
| 0183372 | 10/1985 | European Pat. Off. . |
| 0221570 | 7/1986 | European Pat. Off. . |
| 1706147 | 9/1955 | Fed. Rep. of Germany . |
| 3640745 | 6/1987 | Fed. Rep. of Germany . |
| 2391709 | 12/1978 | France . |
| 2525896 | 4/1983 | France . |
| 03752 | 11/1983 | PCT Int'l Appl. . |
| 1205743 | 9/1970 | United Kingdom . |
| 1565828 | 4/1980 | United Kingdom . |

OTHER PUBLICATIONS

Strecker et al., "Experimentelle Untersuchungen mit einer neuen perkutan einfuhrbaren und aufdehnbaren GefaBendoprothese", Fortshr. Rontgenstr. 147, 1987.
Rousseau et al., Radiology, 164:709, 1987, "Self-Expanding Endovascular Prosthesis: An Experimental Study".
Mullins et al., "Implantation of Balloon-Expandable Intravascular Grafts by Catheterization in Pulmonary Arteries and Systemic Veins"-(Circulation, 77, 188, 1988).
Palmaz et al., "Expandable Intrahepatic Portacaval Shunt Stents", AJR, 145:821, 1985.
Palmaz et al., "Expandable Intraluminal Graft: A Preliminary Study", Radiology, 156:73, 1985.
Palmaz et al., "Atherosclerotic Rabbit Aortas: Expandable Intraluminal Grafting", Radiology, 160:723, 1986.
Maass et al., "Radiological Follow-Up of Transluminally Inserted Vascular Endoprostheses: An Experimental Study Using Expanding Spirals", Radiology, 152:659, 1984.
Sigwart et al., "Intravascular Stents to Prevent Occlusion and Restenosis after Transluminal Angioplasty", New England Journal of Medicine, 316:701, 1987.
Dotter, "Transluminally-Placed Coilspring Endarterial Tube Grafts", Invest. Radiol., 4:329, 1969.
Carrel, "Results of the Permanent Intubation of the Thoracic Aorta", Surgery Gyn. and Obs., XV:245, 1912.

(List continued on next page.)

Primary Examiner—Dalton L. Truluck

[57] ABSTRACT

Mounted on the catheter is an endoprosthesis which can be inserted into a vessel, for example, in a predetermined position, radially expandable, implantable at the expansion site, where it is subsequently retained in place. The endoprosthesis can encompass a section of the catheter by its own radial tension and can thereby be retained in an essentially fixed position, without axial play, while its separation from the catheter is effected by radial expansion during implantation. The endoprosthesis may, however, also be mounted on the catheter in an essentailly fixed position, without axial play, by mechanical means ceasing to be effective after the implantation because of radial expansion, or which can be eliminated after the implantation so as to enable the catheter to be withdrawn.

24 Claims, 3 Drawing Sheets

OTHER PUBLICATIONS

Lawrence et al., "Percutaneous Endovascular Graft: Experimental Evaluation", Radiology, 103:357, 1987.

Rousseau et al., "Treatment of Post-Operative Biliary Stenosis by an Auto-Expansible Metallic Endoprostheses", Italy Meeting, May 27, 1987, p. 8.

Cesarini et al., "Experimental Endovascular Reinforcement", Neuroradiology 28:78, 1986.

Cragg et al., "Percutaneous Arterial Grafting", Radioloby 150:45, 1984.

Sugita et al., "Nonsurgical Implantation of a Vascular Ring Prosthesis Using Thermal Shape Memory Ti/Ni Alloy (Nitinol Wire)", Trans. Am. Soc. Artif. Intern. Organs, vol. XXXII, 1986.

Wright et al., "Percutaneous Endovascular Stents: An Experimental Evaluation", Radiology 156:69, 1985.

Wallace et al., "Tracheobronchial Tree: Expandable Metallic Stents Used in Experimental and Clinical Applications", Radiology 158:309, 1986.

Charnsangavej et al., "Stenosis of the Vena Cava: Preliminary Assessment of Treatment with Expandable Metallic Stents", Radiology 161:295, 1986.

Duprat et al., "Self-Expanding Metallic Stents for Small Vessels: An Experimental Evaluation", Radiology 162:469, 1987.

Rosch et al., "Experimental Intrahepatic Portacaval Anastomosis: Use of Expandable Gianturco Stents", Radiology 162:481, 1987.

German Document numbered 706,147 is of unknown origin.

Nawa et al., "Pulmonary Artery Connection in the Fontan Procedure, " Chest, 91:552, (1987).

Rosch et al., Jama, 259:327, 1988.

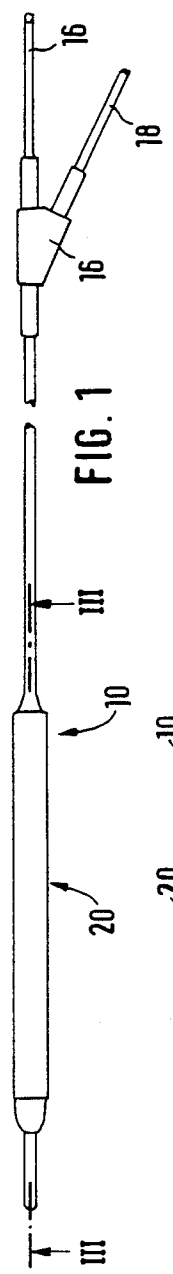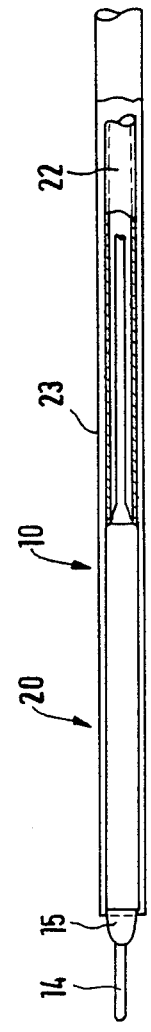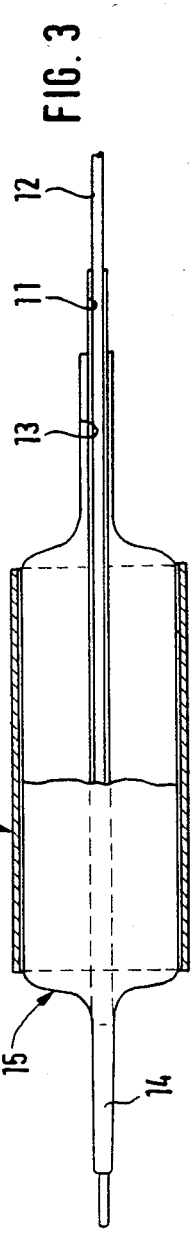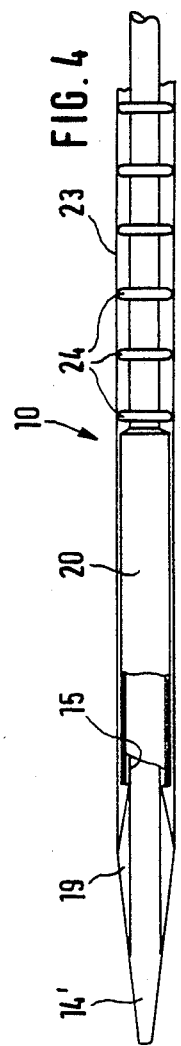

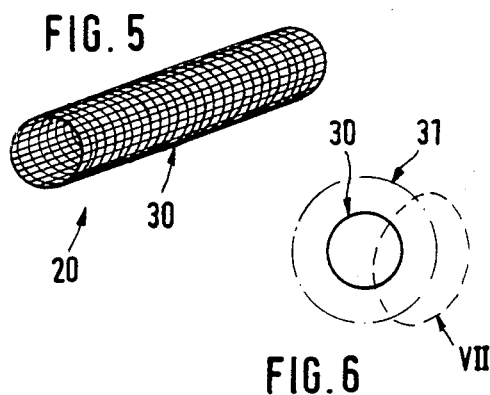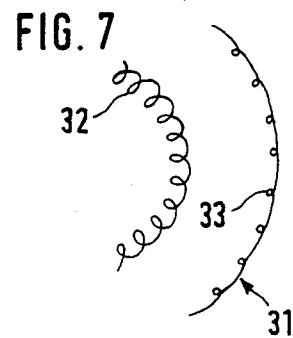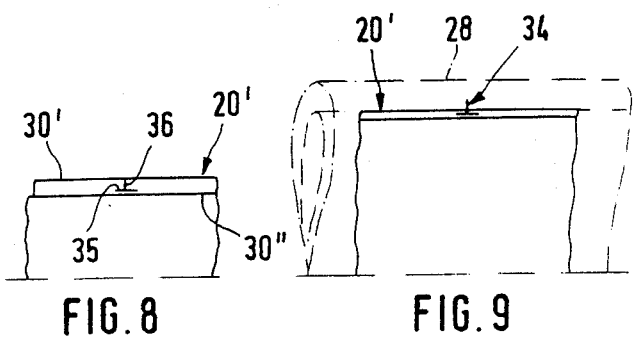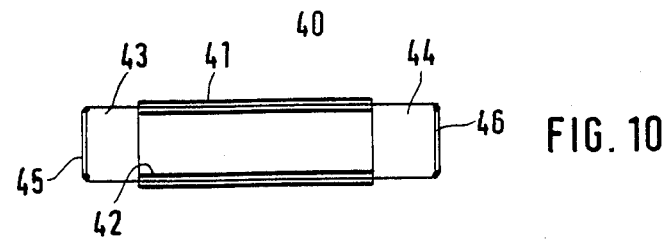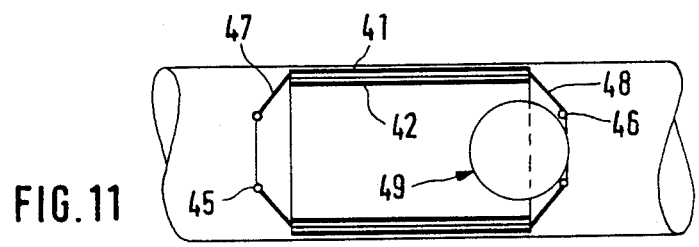

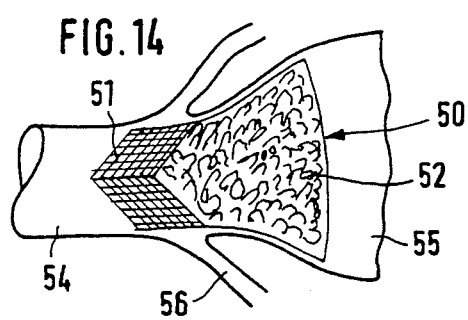
FIG. 14
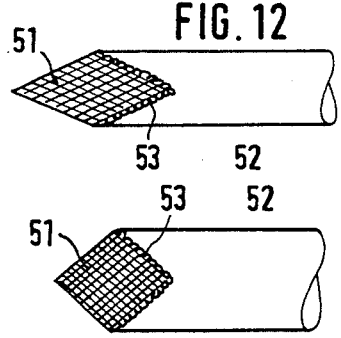
FIG. 12
FIG. 13
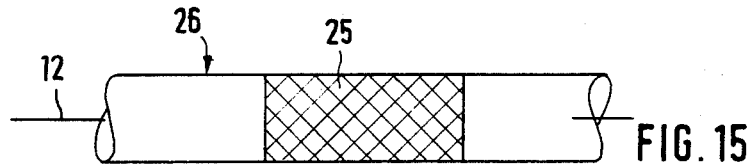
FIG. 15
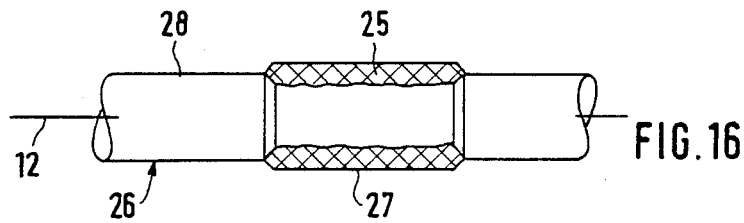
FIG. 16
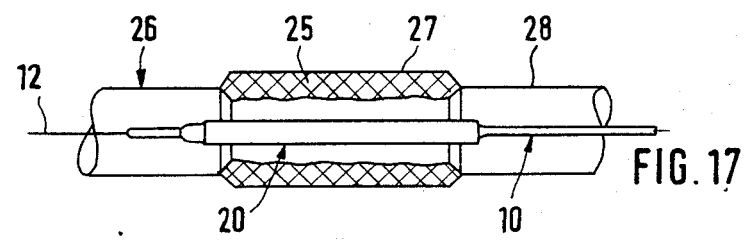
FIG. 17
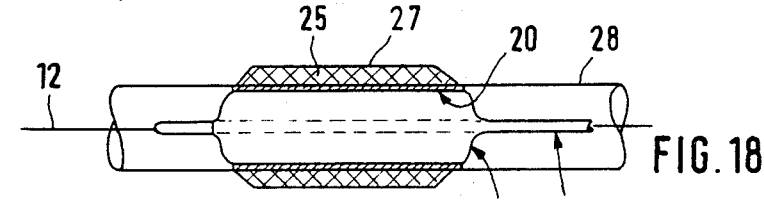
FIG. 18
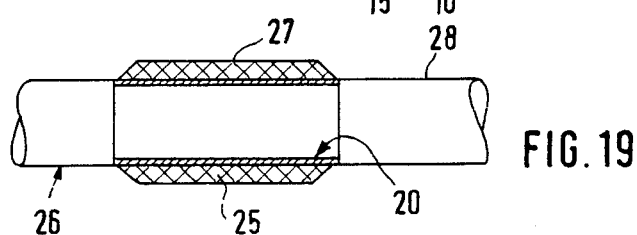
FIG. 19

DILATATION CATHETER

The invention refers to a catheter for establishing and dilating connections to or between body cavities, particularly for opening and dilating vessels.

Dilatation catheters are generally known, particularly as balloon catheters with two lumina (so-called Gruentzig catheters), one lumen of which serves for being slid over a guide wire previously inserted into a vessel narrowed or occluded in sectors by a thrombus, whereas the other lumen ends in a balloon sector of a predetermined axial extension and which is radially expandable through the lumen by the admission of pressure media.

When used in the prescribed manner, a dilatation catheter, is introduced into a vessel and advanced to the region of a thrombus, for example, while the process is visually controlled (by radiography). The thrombus is then be compressed by radial expansion of the balloon section as a result of the admission of a pressure medium which, as a rule, leads to a dilation of the vessel wall surrounding the thrombus.

Catheter recanalization or dilatation of arteries will, however, not always lead to satisfactory results. It was found that particularly in cases of arterial occlusion extending over longer sections, reocclusions are likely to form, or that the arterial wall will partly collapse again as a result of a serious sclerosis of the walls. Moreover, after vascular dilation, hyperplastic vascular reaction narrowing the lumen may occur.

Accordingly, it must be the purpose of the invention to create an improved form of catheter for establishing and dilating passages to or between body cavities, particularly for the opening and dilation of vessels in such a manner as to preclude as far as possible any collapse of the vessel walls, or hyperplastic vascular reactions, even with arterial reocclusions extending over greater lengths.

This task has been solved in that at least one radially expandable endoprosthesis, fixable in its expansion site, can be mounted on the catheter to enable the latter to be withdrawn from the newly formed or dilated passage, as for example, from the thrombus region, whereas the endoprosthesis will remain in its position, thus effectively preventing any reocclusion of the patent lumen.

The invention refers to a catheter fitted with an endoprosthesis that can be percutaneously introduced into a diseased vessel or into an opened passage leading to or existing between body cavities, with the endoprosthesis being expandable after placement and fixable in a predetermined expanding position, and being separable from the catheter which can be withdrawn again.

The application of such an endoprosthesis is by no means confined to the treatment of arterial stenosis but is also possible in cases of phlebothrombosis that cannot successfully be treated by balloon dilatation, for example. Likewise, arterial bypasses, arterviovenous and protocaval shunts can be percutaneously accomplished by using the catheter forming part of the invention. In the same way, an endoprosthetic therapy of an arterial aneurysm of, for example the aorta abdominalis and of the large pelvic arteries is also possible, just as the treatment of other cavities such as bile ducts, urinary tract and of cerebrospinal fluid pathways.

Although there exist reports of animal experiments (Andrew W. Cragg et al., "Percutaneous arterial grafting", *Radiology* 150, 45–49, 1984) where it was tried to insert a radially deformed, helical and spring-like spiral under expanding tension into a vessel, but the pushing ahead of such a spiral inside the catheter lumen did not prove practicable. At the same time, this method called for catheters of undesirably large diameters, nor could the problem of separating from the spirals the means necessary for pushing the latter right through the catheter lumen—after placement of the spirals—be solved.

For the implantation of an endoprosthesis the invention, therefore, suggests the use of a catheter on which a radially expandable endoprosthesis, fixable in its expansion site, is mounted and which can be separated, after its due placement, from the catheter whereupon the withdrawal of the catheter, now released from the endoprosthesis, can be achieved very easily, with the endoprosthesis remaining in its fixed position as an implant.

According to the invention, the endoprosthesis is coaxially firmly mounted on the catheter in such a manner that by pushing the catheter forward into a vessel narrowed by a thrombus, for example, it is possible, on the one hand, to move the endoprosthesis into the region of the thrombus, and after its due placement, a separation of the endoprosthesis from the catheter and the fixation of the endoprosthesis in its expanded state can be assured. In another configuration of the invention the endoprosthesis can be mounted on the catheter with an initial radial tension and so be coaxially fixed on the latter up to its radial expansion and until it is finally separated.

In another configuration of the invention, the endoprosthesis can be coaxially fixed by mechanical means at the side away from the direction into which the catheter is inserted, with a tube slid over the catheter and serving as a means for fixing the endoprosthesis on the latter, or the catheter can be fitted at the side, away from the catheter tip and taking up the endoprosthesis, with a flange-type annular bulge on which the endoprosthesis supports itself on the side axially away from the inserting direction of the catheter. There may also be provided, a thin-walled sheath, slid over the catheter and covering the endoprosthesis end facing the catheter tip or also slightly overlapping that end and which can be pulled off from the endoprosthesis towards the side away from the catheter tip.

Such a sheath may consists of partially rigid plastic material will be suitable, while being introduced into a vessel, for instance, for adapting itself to any vascular curvature and prevents the endoprosthesis—while being inserted through the solid cutaneous tissue—from being damaged by muscular tissue and vessel walls, or from changing its position on the catheter. After placement of the endoprosthesis, the jacket covering the latter is pulled off the endoprosthesis while the endoprosthesis is held in its normal position on the catheter section on which it is mounted and where it can be implanted by subsequent radial expansion and by the fixation its expanded state.

Another configuration of the invention suggests a design of the endoprosthesis as a radially expandable cuff which be thereafter be locked in its intended expanded state.

In another important configuration of the invention, the endoprosthesis is a tubular structure of metal or plastic filaments, each of good biocompatibility, assembled by knitting, crocheting or the like, radially expandable and remaining unchanged in its expanded state. Apart from knitting or crocheting, any other formation of meshes may be used for producing such endoprostheses within the meaning of the invention.

Tubular knitted structures are, for example, known for the assembly of filters, although they were, so far, not used as radially expandable endoprostheses remaining unchanged at their expansion site. Thorough tests, however, have demonstrated the specific usefulness of knitted or crocheted or differently produced endoprostheses assembled by the formation of meshes because they can, on the one hand, be implanted in a most simple manner into cavities of the body, and because they possess, on the other hand, the elasticity needed for implants.

Such implants will, because of their own resilience, return to their normal unexpanded state after a limited deformation caused by outside forces, for example with the result that the risk of renewed obstructions forming within the region of such implants is essentially reduced.

Another important advantage of an endoprosthesis assembled as described is explained by the fact that the same is steplessly and radially expandable within predetermined limits and can so be easily adjusted to prevailing conditions in any application. This particularly applies if, in the event of a further development of the invention, the endoprosthesis is radially deformed before its intended use and reduced in diameter in such a manner that the individual meshes will interlock with some clearance.

According to another useful development, the radially expandable endoprosthesis formed as a tubular structure consists of not less than two layers, produced by knitting, crocheting or the like, encompassing each other and which may also be designed in different ways. Accordingly, the resistance of such endoprostheses to deformations caused by outside forces can be chosen by selecting the number of layers in accordance with the intended purpose.

The development described here can also be characterized by anchoring means penetrating by radial expansion of the endoprosthesis, its outer layer, and by the anchoring means being connected to an inner layer, and by anchoring pins radially extending from the latter may appear which, in the expanded state, will stretch through the outer layer and engage with a vessel wall or with the tissue surrounding a body cavity.

The tubular structure forming the endoprosthesis may also made of a filament material consisting of not less than two single filaments combined to form a cord and jointly consisting of single filaments processed by knitting, crocheting or looping. Endoprostheses so produced excel by high resistance to any deformation caused by outer forces.

Another development of this configuration is characterized by a plastic deformation of the filament material within the region of the meshes during radial expansion of the endoprosthesis.

According to another configuration, the filament material from which the endoprosthesis is produced, can be provided with a coating of a material of good biocompatibility. The flexible tubular structure produced by knitting, crocheting or the like may also be provided, outside and/or inside, with a cuff-like covering of flexible material impermeable to liquids, e.g., Latex.

Another likewise important configuration of the invention is characterized by the formation of the endoprosthesis as a vascular valve with tubular segments coaxially extending along both sides of and beyond the tubular structure made by knitting, crocheting or the like and which are fitted, at their ends, with non-expandable retaining rings, one of the segments being provided with a lining or coating impermeable to liquids e.g., Latex of another suitable material. When such a vascular valve is implanted, the non-expandable retaining rings cannot take part in the process of radial expansion with the result that at both sides of the tubular central section, retaining baskets are formed, one of the latter being provided with a lining or coating impervious to liquids, to be introduced jointly with a valve sphere into the implanted vascular valve which produces an optionally tight closure whereas, in the region of the other end segment, even with the valve sphere located close to the retaining ring, a closure cannot be effected in the absence of a coating or lining impervious to liquids.

Another advantageous configuration of the invention is characterized in that the endoprosthesis designed as a semilunar valve or as an aortic valve, for example, is formed by not less than two rhomboid valves arranged at one end of atube section made by knitting, crocheting or the like, the valves consisting of a fine-meshed web whose interwoven filaments run approximately parallel with each of two rhomboid edges, the valves being taken up in triangular segments of the tube section, with one each of the diagonals running approximately in the axial direction of the tube section and being connected alongside two rhomboid edges with the edges of the triangular segments in the tube section, as by sewing up or crocheting with the aid of spring wire.

Such a semilunar valve can be implanted into cardiac chambers in such a manner that the valves inserted into triangular segments of the tubular sections are located in the region of the origins of the coronary arteries, whereas the tube section extends right into the ventricle where it is implanted and duly placed by radial expansion, to be fixed, if required, by suitable anchoring means.

The valves of this endoprosthesis consists of a fine-meshed web, the gaps of which are, in the implanted state, agglutinated with blood clots or can be sealed off by silicon.

The endoprosthesis described here can also be implanted reversely, with its tube section extending into the aorta, not into the ventricle. Considering that the tube section made by knitting, crocheting or the like is, near the valve, cut out triangularly, implantation must be effected so that the origins of the coronary arteries are exposed. Any loss of elasticity can easily be compensated by a spring wire forming a seam between valves and tube section and which, in the implanted state, additionally presses the tube section and the valves against the vessel wall. Besides, the valves are rounded off at their tips and,—in the implanted state-,—at the edges close to the wall of the aorta.

If, according to another important configuration of the invention, the endoprosthesis is mounted on a balloon section which is radially expandable after admission of a pressure medium, above a lumen ending in this balloon section, the coaxial fixation of the endoprosthesis on the catheter on the one hand, and the separation of the endoprosthesis from the catheter after due implantation on the other hand, can be effected most conveniently by the admission of a pressure medium to the balloon section of the catheter, in the usual way, expanding the balloon section radially in such a manner that the endoprosthesis mounted on the catheter in the region of the balloon section is subjected to radial expansion to a predetermined extent, in order to be fixed in position in that predetermined expanded state.

The configuration described here is considered to be of special value because catheters, with a balloon section radially expandable, are generally known and have stood the test. It will be advisable to use such a catheter with a lumen to be inserted along a guide wire.

It has proved particularly advisable to use, in accordance with another configuration, a catheter with a cone slightly rising in the region between balloon section and catheter tip. This will prevent the formation of a step normally present within such circumstances in the region between catheter tip and balloon section, and will thus greatly facilitate the introduction of the catheter into a vessel. The aforesaid cone may also be linked with a cone descending towards the balloon section, which can, for example, limit the movement of a sleeve covering the endoprosthesis mounted on the balloon section and which can be withdrawn so as to release the implant.

A cone descending or dropping off towards the balloon section of the catheter will also diminish the danger of an expanded implant getting caught in the region of a curvature when the catheter is withdrawn.

According to the attached drawings a balloon catheter of the invention with a radially expandable endoprosthesis mounted on the balloon section and fixable in its expansion site, will be described, with a possible configuration of such an endoprosthesis and the opening of a vessel occluded by a thrombus and, in this connection, the implantation of an endoprosthesis in the region of the thrombus in the vessel. The schematic views show:

FIG. 1: a catheter with a radially expandable balloon section and an endoprosthesis mounted on the same without axial play and fixable in a predetermined expansion site, FIG. 2: a catheter as described in FIG. 1 but with a tube partly shown in its longitudinal section and pushed-on over the catheter, with the endoprosthesis mounted on the balloon section supporting itself on the tube at the side away from the inserting direction, and with a thin-walled sleeve covering the endoprosthesis up to the end facing the catheter tip and which, encompassing the tube pushed over the catheter, stretches and extends at the side of the endoprosthesis away from the catheter tip.

FIG. 3: the radially expanded endoprosthesis, shown according to a longitudinal section III—III in FIG. 1, fixed at the expansion site, and the catheter with the balloon section, also expanded and partly shown in profile, FIG. 4: a catheter, in a view as shown in FIG. 2, modified with a double cone in the region of the catheter tip and with spacing means, in the region extending from the balloon section to the side away from the tip, FIG. 5: an endoprosthesis, formed as a tubelike knitted structure, shown by itself, before radial expansion, FIG. 6: a cross section of the endoprosthesis, according to FIG, 4, in unbroken lines in the non-expanded state and in dash-and-dot lines after expansion, FIG. 7: in an enlarged segment according to VII, according to FIG. 6, the formation of the meshes of the knitted structure in the original position before radial expansion and at the expansion site, FIG. 8: in a longitudinal sectional view, an enlarged segment of a non-expanded endoprosthesis with two knitted layers encompassing one another and with anchoring means fastened to one of the knitted inner layers, with the anchoring means provided with the anchor pin inside the annular gap between the knitted layers and radially extending outwards.

FIG. 9: in a view according to FIG. 8, the axial fixation of the endprosthesis due to contacts with the anchor pins piercing the outer layer of the knitted structure and engaging the tissue wall, FIG. 10; an endoprosthesis formed as a vascular valve, shown by itself, before radial expansion, in a longitudinal sectional view, FIG. 11: the vascular valve according to FIG. 10. in the implanted state inside an assumed vessel, likewise in a longitudinal sectional view.

FIG. 12: a vascular valve formed as an aortic valve, shown by itself, in the non-expanded state, FIG. 13: the aortic valve according to FIG. 12, in the radially expanded state, FIG. 14: an aortic valve implanted in the region of the origin of the coronary arteries, FIG. 15: a vessel occluded by a thrombus, with a guide wire inserted into it, shown in a longitudinal section of the vessel, FIG. 16: in a view according to FIG. 15, showing the vessel after a balloon catheter canalization with the thrombus in a compressed state, FIG. 17: in a view according to FIG. 15, a balloon catheter with an endoprosthesis mounted on the balloon section, in the region of the compressed thrombus, before radial expansion of the balloon section and of the endoprosthesis, FIG. 18: likewise in a view according to FIGS. 15 through 17, with the endoprosthesis compressed against the vessel wall by radial expansion of the balloon section of the catheter, caused by the admission of pressure media, and FIG. 19: the endoprosthesis, shown in a longitudinally sectional view throughout the vessel, implanted in the same, in the region of the compressed thrombus, after the removal of the balloon catheter and of the guide wire inserted into the vessel.

Catheter 10, shown in a diagrammatic view in FIGS. 1 through 4, represents a known catheter with two lumina whose central lumen 11 extends axially through the catheter and and which serves for sliding the catheter upon a guide wire 12, as shown in FIG. 3. A second lumen, concentrically encompassing the first lumen, ends in a balloon section 15 arranged close by the catheter tip 14. Lumina 11, 13 extend coaxially approximately the whole axial extent of the catheter, to branch out in an angular piece 16 arranged endwise. Central lumen 11, to be slid on guide wire 12, is in alignment with conduit 17 extending endwise from the angular piece, in alignment with the catheter. Lumen 13 ending in balloon section 15, is in flowing connection with line 18 which runs in a direction forming an angle with line 18.

As distinct from previously known balloon catheters, the invention is characterized by an endoprosthesis 20, mounted essentially without axial play on the balloon section, which is radially expandable after the admission of pressure media, with the endoprosthesis being implantable, as described below, after radial expansion, in a vessel, for example, and being separable from the catheter.

The endoprosthesis can be mounted by its own radial tension on catheter 10 and thereby be coaxially fixed on the latter and separable from the catheter as a result of radial expansion and after fixation at the expansion site.

Instead of the coaxial fixation of the endoprosthesis on the balloon section 15 of catheter 10 by its own radial tension or in addition to the latter, endoprosthesis 20 can also support itself on tube 22 previously slid on the catheter at the side away from the inserting direction. This is illustrated by FIG. 2.

FIG. 2 also shows a sheath 23 concentrically encompassing endoprosthesis 20 over its full length, extending beyond it at the side away from the catheter tip 15 and protecting the endoprosthesis from any damage caused during the insertion of catheter 10 through the skin, the muscles or the vessel walls, and also from migrating on the catheter. The tubelike sheath consists of a thin-walled plastic material having a good stability of shape, and is capable of adjusting itself well to any curvatures of the inserting paths and will, after due placement of the endoprosthesis, be withdrawn from the same to the side away from the catheter tip, in the course of which the tube supporting the endoprosthesis and whose remote end surpasses the sheath by at least the length of the endoprosthesis, remains in its supporting position as can be seen from FIG. 2.

With catheter 10' as illustrated in FIG. 4, a double cone 19 is arranged between catheter tip 14' and balloon section 15, with the endoprosthesis 20 mounted on the same. Thereby the step occurring at catheter 10 according to FIGS. 1 through 3 between catheter tip and balloon section is avoided and the insertion into the vessel is facilitated. The balloon catheter is fitted at the side away from the balloon section and in the longitudinal direction of the catheter, with spacing rings 24 (arranged with spaces between same) while on the rings, sheath 23, slid over the endoprosthesis in the same way as with the catheter shown in FIG. 2 and extending beyond the endoprosthesis, radially supports itself. Moreover, rings 24 located close to the balloon section, holds the endoprosthesis in its coaxial position on the balloon section.

Balloon catheters of the type described here serve for opening and/or dilating vessels, occluded or narrowed by thrombi, for example. FIG. 15 shows in a schematic view a vessel 26 occluded by a thrombus 25. In order to open such a closed or only narrowed vessel, a guide wire 12 must, first of all, be inserted into the vessel whereupon a balloon catheter with one of its lumina located about the guide wire 12 is advanced inside the vessel in such a manner that the balloon section 15, radially expandable after the admission of pressure media through the other lumen, is located in the region of the thrombus. By radial expansion of the balloon section as a result of admission of pressure media through the first lumen, thrombus 25 is radially compressed, this leading to expansion 27 of vessel wall 28, as illustrated by the schematic view of FIG. 16 into the region of the compressed thrombus.

With the known balloon recanalization the catheter and the guide wire are then withdrawn from procedure, the vessel, after the elimination of the pressure media causing radial expansion of the balloon section. This may, however, lead in the course of time to repeated vascular occlusion. Accordingly, the catheter suggested by the invention allows the implantation in the region of the compressed thrombus of endoprosthesis 20 in order to prevent a reocclusion or another angiostenosis.

Accordingly, after the balloon recanilization described above and after elimination of the pressure media acting on the balloon section, the catheter is withdrawn from vessel 26, leaving guide wire 12 in its place while a catheter, as described by the invention, accommodating on its balloon section an endoprosthesis 20, radially expandable and fixable at a predetermined expansion site, is slid on guide wire 12 until the balloon section with the endoprosthesis mounted on it, reaches the region of the compressed thrombus 25 in the vessel. This is shown by FIG. 17.

After endoprosthesis 20 mounted on the balloon section 15 of the catheter has been positioned inside vessel 26, the endoprosthesis is radially expanded by the admission of pressure media to balloon section 15 of the catheter and compressed inside against the vessel wall 28 with the result that thrombus 26, already precompressed, and the vessel wall surrounding it undergo an additional radial expansion. The endoprosthesis is held firmly in position in the expanded state as shown in FIG. 18, as described more fully below.

After the fixation of the endoprosthesis in its position compressed against the wall, balloon section 15 of the catheter is radially reduced after the elimination of the pressure media, and the catheter is withdrawn, along with guide wire 12, from vessel 26. The endoprosthesis 20 remains in the vessel as an implant and so prevents any retrogression of the compressed thrombus 25 and the danger of a renewed angiostenosis or of a reocclusion.

Some suggested configurations of the endoprosthesis, firmly mounted on balloon section 15 without axial play, and also radially expandable after radial expansion of the balloon section and fixable at a predetermined expansion site to prevent any subsequent cross-sectional reduction are shown by FIGS. 5 through 11.

The configuration of endoprosthesis 20, shown by FIGS. 5 through 9 shows a tubelike knitted structure 30 of metal wires or plastic filaments, each of good bicompatibility, in a diameter range of approx. 0.1 mm, produced by tightly fitting knitting work around a core (not illustrated here) which can subsequently be removed. The cross-sectional view according to FIG. 6 shows in unbroken lines the endoprosthesis, according to FIG. 5, in its original state, i.e. before expansion, whereas the expanded state is illustrated by dot-and-dash lines. The tubelike knitted structure 30 forming the endoprosthesis represents a loose knitted shape in its original state, i.e. before radial expansion, whose individual meshes 32 interlock loosely, with some clearance between them, similar to the looped pattern as shown in FIG. 7. The loose interlocking of the individual meshes can, if required, be improved by a compression of the knitted structure and by a simultaneous reduction of the diameter before it is used an endoprosthesis. During radial expansion of the knitted structure the loops forming the individual meshes are deformed beyond the elastic limits of the filament material, this being equal to a plastic deformation of the filament material until the loops have adopted a shape as roughly indicated by item 33 of FIG. 7.

In view of the plastic deformation of the filament material forming the meshes and occuring during radial expansion of the tubelike knitted structure, an automatic fixation takes place in the given expanded state without the need of any additional measures to be taken. Accordingly, the tubelike knitted structure is within predetermined limits variably expandable and hence widely adjustable to the requirements of any specific case of application.

Instead of tubelike knitted structures, endoprostheses made by crocheting, weaving, knotting or by other means, of filament material, may be used.

The diagrammatic configuration illustrated by FIGS. 8 and 9 shows an endoprosthesis 20' made of two knitted layers 30', 30" encompassing each other, and anchoring means taken up between them, with a pressure plate 35 fastened to the inner knitted layer 30", and an anchoring pin 36 extending from it radially in an outward direction. As shown by FIG. 8, the anchoring pins extend before radial expansion of the endoprosthesis in an annular gap 37 between the knitted layers 30', 30" but penetrate the outer knitted layer 30' during radial expansion, finally engaging in vessel wall 28 shown in FIG. 8 and indicated there by dot-and-dash lines. A form-fit fixation of the endoprosthesis in the vessel wall will thereby be assured.

The endoprosthesis illustrated in FIGS. 10 and 11 represents a vascular valve 40 with a tubular mid-section consisting of two knitted layers encompassing each other, and of two tubular sections 43,44 made of expandable material, with both ends axially extending beyond the knitted layers and firmly connected, at both ends, with non-expandable retaining rings 45, 46. Sections 43, 44 may also represent knitted layers, with one of the sections, section 44 for example, being covered by a lining or coating impermeable to liquids, as with latex, for example.

The implantation of the vascular valve is effected in the manner described above in conjunction with endoprosthesis 20, while the balloon section of the catheter to be inserted shall not exceed the axial length of the knitted layers 41, 42 nor project from the latter at any side. When the vascular valve, after having been placed in correct order in a vessel, is radially dilated by the application of pressure of the balloon section of the catheter, retaining rings 45, 46 located at both ends of the axially projecting sections 43, 44 will not take part in the expansion process, with the result that a both ends of the knitted layers, a proximal and a distal retaining basket 47, 48 will be formed, as shown in FIG. 11.

After implantation of the vascular valve and the withdrawal of the catheter from the vessel, a detachable tube forming a spherical sheath is inserted into the vessel and introduced through one of the retaining rings into the implanted vascular valve 40 and subsequently expanded to a spherical shape after the admittance of silicon or similar material, with the result that, after the detachment of the feeding tube, valve ball 49 is formed in the vascular valve. In view of the lining or coating of the segment forming retaining basket 48, ball 49 in combination with retaining basket 48, tightly closes the vessel. In the region of retaining basket 47, however, a vessel closure cannot be effected, even when ball 49 rests closely against basket 47, because segment 43 is not provided with a lining or coating.

The endoprosthesis shown in FIGS. 12 through 14 represents an aortic valve 50 with three rhomboid valves 51 grouped at one end of a tubular section 52 made by crocheting, knitting or the like, each of them being connected, with the diagonals running in the axial direction of the tubular section along two rhombus edges to the edges of triangular segments in the tubular section, by sewing up or by crocheting, as indicated by 53 in FIGS. 12 and 13.

FIG. 12 shows an aortic valve by itself before radial dilation, with only one of the three rhomboid valves 51 mounted in triangular segments of tubular section 52 being visible and whose main diagonals extend in the longitudinal direction of the tubular section. Valves 51 consist, for example, of a finely meshed web of woven wires whose wires crossing each other run in parallel with two rhombus (diamond) edges. FIG. 13, on the other hand, illustrates aortic valve 51 in the radially dilated state in which the rhomboid valves connected with two rhombus edges to the segment edges of the tubular section 53, have adopted an approximately quadratic shape, as viewed from above. The tubular section formed by crocheting, knitting or the like is radially expandable in the same way as the endoprosthesis described above and can, at its expansion site, be fixed in position by plastic deformation of the looped structures. In order to permit a fixation in due position, additional anchoring means can be provided, as described above with reference to FIGS. 8 and 9. The rhombus-shaped valves of finely meshed web, linked up with the tubular section, will easily adjust themselves during radial expansion of the tubular section to the latter because the filaments of the finely meshed web, crossing each other are running in parallel with two rhombus edges, and because the main diagonal of the rhombus (or diamond) extends in the longitudinal sense of the tubular section. In view of such information and grouping of the valves, the latter will, with the progressive radial expansion of the tubular section, gradually change from the rhombus-shaped form into the quadratic form, as shown in FIGS. 12 and 13.

FIG. 14 finally illustrates the aortic valve 50, implanted through an aorta 54, whose radially expanded tubular section projects into a cardiac chamber 55 where is is fixed in position in a manner that is actually of minor interest, while valves 51 are located in the region of the origins 56 of the coronary arteries. The implant is, at the same time, fixed in such a manner that in view of the triangular segment of the tubular section, at its end near the valve, the origins of the coronary arteries remain free and unobstructed.

What is claimed is:

1. A tubular endoprosthesis device having a wall structure comprised of an open fabric of loosely interlocked loops of filament material, the device having a first relatively small diameter form for low profile introduction to a body passageway while encircling a radially expandable section of a catheter, said loops being capable of progressive permanent deformation with attendant radial expansion of the open fabric in response to increasing expansion of said expandable section of the catheter.

2. A catheter having an expandable section, and a tubular endoprosthesis device disposed on said catheter, surrounding said section, the wall structure of said device being comprised of an open fabric of loosely interlocked loops of filament material, said loops being capable of progressive permanent deformation, with attendant radial expansion of the open fabric from a first relatively small diameter form, in response to increasing expansion of said expandable section of said catheter.

3. The invention of claim 1 wherein said wall structure of said endoprosthesis device in its said first, small diameter form comprises a radially inwardly deformed interlocking loop structure, there being clearance between interlocking loops of said wall.

4. The invention of any of claims 1, 2 or 3 wherein said tubular wall structure in its first, small diameter form, is in a radially shaped, reduced-diameter state relative to its as-formed state.

5. The invention of claim 1, 2 or 3 wherein said fabric of loosely interlocked loops is constructed such that said radial expansion occurs without change of the axial length of said endoprosthesis device.

6. The invention of claim 1, 2 or 3 wherein said wall structure formed of loosely interlocked loops comprises an open knit fabric.

7. The invention of any of the claims 1, 2 or 3 wherein said wall structure formed of loosely interlocked loops comprises an open crocheted fabric.

8. The invention of any of the claims 1, 2 or 3 wherein the filaments of said loosely interlocked loops comprise metal wire selected to enable progressive permanent deformation of said loops in response to increasing expansion of said expandable catheter section.

9. The invention of any of the claims 1, 2 or 3 wherein the filaments of said loosely interlocked loops comprise plastic filaments selected to enable progressive permanent deformation of said loops in response to increasing expansion of said expandable catheter section.

10. The invention of any of the claims 1, 2 or 3 wherein said wall of said endoprosthesis includes a biocompatible liquid-impermeable layer.

11. The invention of claim 10, wherein said liquid impermeable layer comprises a cuff-like covering positioned inside or outside said open fabric.

12. The invention of claim 1, 2 or 3 wherein said endoprosthesis is constructed and arranged to be placed in a blood vessel of a patient to provide support to the wall thereof.

13. The invention of any of claims 1, 2 or 3 wherein said wall structure of said endoprosthesis comprises an inner and an outer layer of filament material.

14. The invention of claim 13, wherein said endoprosthesis includes an anchor held within said outer layer of said endoprosthesis, said anchor being capable of penetrating said outer layer of said endoprosthesis upon expansion of said endoprosthesis.

15. The invention of claim 14, wherein said anchor is linked to said inner layer of said endoprosthesis by an anchor pin radially extending from said inner layer.

16. The invention of any of claims 1, 2 or 3 wherein said wall structure of said endoprosthesis is formed from a filament like material comprising side-by-side filaments forming a cord.

17. The invention of any of claims 1, 2 or 3 wherein said endoprosthesis comprises two cone-shaped segments axially extending, respectively, from the ends of said endoprosthesis, said segments comprising loops of filament material and each having at its end a non-expandable retaining ring, one of said segments including a lining or coating of liquid impervious material.

18. The invention of any of claims 1, 2 or 3 wherein said endoprosthesis comprises two rhomboid-shaped valves at one end of said endoprosthesis said valves comprising a fine-meshed web having interwoven filaments running approximately parallel with one arm of the edges of the valve wherein said valves are positioned along the axial direction of said endoprosthesis and are connected along two edges with an edge of the endoprosthesis.

19. The invention of claim 2 wherein said catheter includes a passage suitable for continuous administration of medication.

20. The catheter of claim 2 wherein said expandible section of said catheter comprises a balloon.

21. The invention of claim 2 wherein an axially removable thin-walled sheath lies over at least part of said endoprosthesis, securing said endoprosthesis on said catheter.

22. The invention of claim 21 wherein said sheath is adapted to be pulled axially off of said endoprosthesis.

23. In a tubular endoprosthesis device having a wall structure comprised of filament material, the device having a first relatively small diameter form for low profile introduction to a body passageway while encircling a radially expandable section of a catheter, said device being radially deformable by expansion of the catheter section from said first form to a permanent, radially expanded form, said device in said expanded form being capable of maintaining engagement with the bounding wall of said passageway, the improvement wherein the wall structure of said device is comprised of a tube-like, knitted open fabric of loosely interlocked loops of metallic filament material, said tube-like fabric being radially inwardly deformed relative to its as-knit form and having clearance between loops, said loops being capable of progressive permanent deformation with attendant radial expansion of the open fabric in response to increasing expansion of said expandable section of the catheter.

24. The device of claim 23, wherein said filament material is in the order of 0.1 mm. in diameter.

* * * * *

UNITED STATES PATENT AND TRADEMARK OFFICE
CERTIFICATE OF CORRECTION

PATENT NO. : 4,922,905

DATED : May 8, 1990

INVENTOR(S) : Strecker

It is certified that error appears in the above-identified patent and that said Letters Patent is hereby corrected as shown below:

Col. 1, line 58; "arterviovenous" should be --arteriovenous--.
Col. 6, line 53; insert "along" after "coaxially".

Col. 7, line 37; insert "--,--" after "same)".
Col. 7, line 42; change "holds" to --hold--.

Col. 8, line 57; insert --as-- after "used".
Col. 8, line 58; insert --,-- after "structure".
Col. 9, line 32; delete "as with" after "liquids,"
Col. 10, line 30; "information" should be --formation--.
Col. 10, line 34; "in" should be --by--.

Signed and Sealed this

Twenty-third Day of June, 1992

Attest:

DOUGLAS B. COMER

*Attesting Officer*   Acting Commissioner of Patents and Trademarks